United States Patent [19]

Cubbison, Jr.

[11] Patent Number: 4,849,851

[45] Date of Patent: Jul. 18, 1989

[54] STATIC ELECTRIC DISCHARGE APPARATUS WITH ACTIVE ELECTRICAL CIRCUIT

[75] Inventor: Richard J. Cubbison, Jr., Westminster, Colo.

[73] Assignees: American Telephone and Telegraph Company, New York, N.Y.; AT&T Information Systems Inc., Morristown, N.J.

[21] Appl. No.: 265,153

[22] Filed: Oct. 31, 1988

[51] Int. Cl.$^4$ .............................................. H05F 3/02
[52] U.S. Cl. .................................... 361/212; 361/220; 361/232
[58] Field of Search ............... 361/212, 213, 220, 223, 361/224, 225, 229–232

[56] References Cited

U.S. PATENT DOCUMENTS

| | | | |
|---|---|---|---|
| 3,875,461 | 4/1975 | Richardson et al. | 361/230 |
| 3,993,932 | 11/1976 | Weigl | 361/224 |
| 4,048,667 | 9/1977 | Brennecke | 361/213 |
| 4,107,755 | 8/1978 | Kiefer | 361/220 |
| 4,459,633 | 7/1984 | Vandermark | 361/220 |
| 4,475,141 | 10/1984 | Antonevich | 361/220 |
| 4,570,200 | 2/1986 | Osada et al. | 361/212 |
| 4,586,106 | 4/1986 | Frazier | 361/212 |
| 4,618,909 | 10/1986 | Sanders | 361/212 |

Primary Examiner—L. T. Hix
Assistant Examiner—Brian W. Brown
Attorney, Agent, or Firm—John C. Moran

[57] ABSTRACT

Apparatus for discharging static electricity from the human body by ionizing air and utilizing the flow of ions from the apparatus into the surrounding environment to discharge the body. The apparatus utilizes two power supplies to raise two embedded electrodes positioned in a horizontal plane different voltage potentials with respect to the body. The air is ionized by utilizing discharge electrodes of the opposite polarity positioned over each of the embedded electrodes which results in air ions being formed in a ion distribution above each embedded electrode. The embedded electrodes are positioned a predetermined distance from each other in the embedded plane. Within the region between the embedded electrodes, the ions recombine to form air molecules. The ions in the distribution layers above each embedded electrode drift toward this region under attraction from each other. As the ions move, ions of the same polarity as the body as repelled into free air by virtue of the presence of the static charge on the body. In free air, they eventually drift to a grounding point within the environment. This expulsion of the ions of the same polarity as the body discharges the static electricity from the body.

3 Claims, 1 Drawing Sheet

STATIC ELECTRIC DISCHARGE APPARATUS WITH ACTIVE ELECTRICAL CIRCUIT

TECHNICAL FIELD

This invention relates to the discharging of static electricity from the human body. In particular, it relates to the use of an electrical circuit to ionize air so that the flow of ions results in the static electricity being dissipated from the human body.

BACKGROUND OF THE INVENTION

In many industrial fields, damage can result from the discharge of static electricity from a human body to equipment or components. In certain industries such as the petrochemical and munition industries, the result of such a discharge can be an explosion which not only threatens equipment, but human life. In other industries such as the electronics industry, the discharge of static electricity from a person's body to equipment or components results in damage to that equipment. This is particularly true if the equipment contains MOS components. In the case of the petrochemical and munition industries, very stringent procedures are followed in attempting to avoid the discharge of static electricity which could result in a spark causing an explosion. In the electronic industry, procedures such as grounding the workers are implemented to eliminate such discharges. These procedures are difficult to maintain and at times are ineffective due to worker forgetfulness or the difficulty of eliminating static electricity. The problem with grounding workers is that it limits the mobility of the workers. Also, problems arise from workers forgetting to attach their ground wire to the designated terminal.

SUMMARY OF THE INVENTION

A technical advancement is achieved by an apparatus and method in which a self powered electrical circuit is used to dissipate the static electric charge on a human body directly into the air without requiring a solid or liquid electrical connection to a ground point. The apparatus comprises elements which cause a volume of air near the body to be ionized and utilizes the flow of air ions away from the body to discharge static electricity on the body below a safe potential.

Advantageously, the apparatus provides for the body being at either a negative or a positive potential with respect to ground. The apparatus utilizes buried electrodes to minimize the electrical arcing problem and yet allows the ions to be sufficiently excited so as to discharge the static electricity from the body.

Advantageously, the electric power for the apparatus is provided by self-contained solar cells which are capable of producing the necessary electrical current from ambient light.

DETAILED DESCRIPTION

Figure 1:
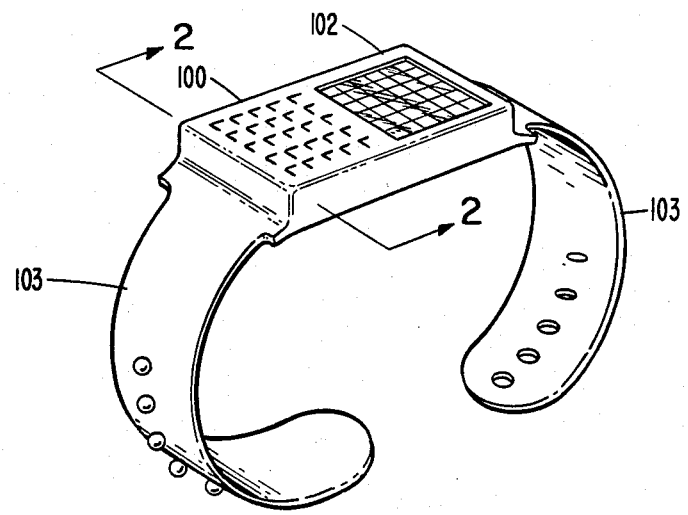
FIG. 1 illustrates the discharge unit capable of being worn on the wrist of a person.

FIG. 1 illustrates the apparatus for discharging static electricity from a human body. The unit illustrated in FIG. 1 is designed to be worn on the wrist; however, it would be obvious to one skilled in the art that other arrangements could be derived so that this unit could be positioned on other portions of the body. The unit illustrated in FIG. 1 consists of discharge unit 100 and solar unit 102 both connected to wrist strap 103. The wrist strap 103 is of a conductive material such as a metal expansion band similar to those worn on a wrist watch or fabricated out of a material rendered conductive by metal threads or conductive impregnation as is done in conventional wrist straps through which workers are electrically grounded to their work benches. Solar unit 102 comprises two subunits each capable of producing the necessary voltage and current. It would be obvious to one skilled in the art that solar unit 102 could be replaced by batteries with the necessary electrical circuits to generate the required voltage. Discharge unit 100 uses electrical power from solar unit 102 to discharge static electricity from the wearer of the apparatus by generating air ions and then allowing the static electricity to dissipate by the flow of ions to a ground point through the air.

Figure 2:
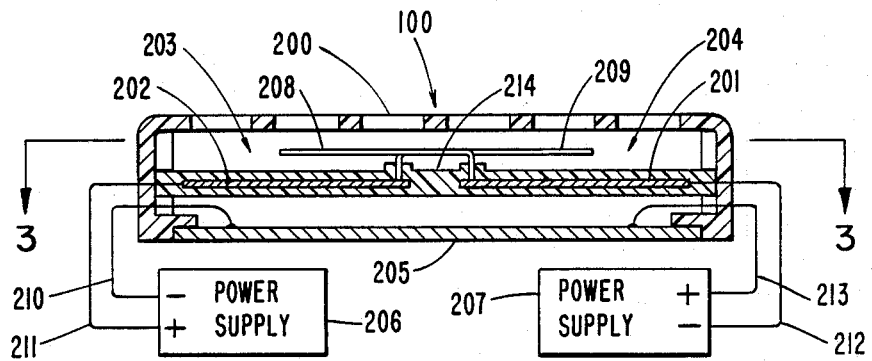
FIG. 2 illustrates a side view of the discharge unit of FIG. 1.

Discharge unit 100 is shown as a side view in FIG. 2. The two subunits of solar unit 102 are illustrated as power supplies 206 and 207. The human body can either be positive or negative with respect to ground, and discharge unit 100 allows for this possibility by the utilization of two power supplies each at a different polarity from the human body which is connected to discharge unit 100 via metal body contact 205. Power supply 206 places embedded positive electrode 202 at a positive potential with respect to the body. This potential of power supply 206 can advantageously be 1500 volts. The negative terminal of power supply 206 is connected to contact 205 via conductor 210, and the positive terminal of power supply 206 is connected to electrode 202 via conductor 211. Similarly, power supply 207 places embedded negative electrode 201 at a negative potential with respect to the body. This potential advantageously can also be 1500 volts. The positive terminal of power supply 207 is connected to contact 205 via conductor 213, and the negative terminal of power supply 207 is connected to electrode 201 via conductor 212. The embedded electrodes are in a horizontal plane with respect to each other separated by region 214. The embedded electrodes are enclosed in a plastic insulation so as to prevent arcing through region 214, which would create a sparking hazard, and to allow the creation of ion distributions 203 and 204 which occupy the space above embedded electrodes 202 and 201, respectively. The relative positioning of the embedded electrodes is illustrated in a top view in FIG. 3.

Figure 3:
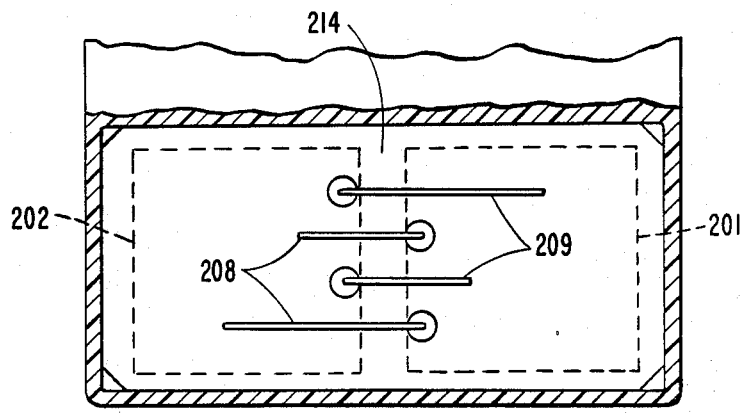
FIG. 3 illustrates a top view of the discharge unit of FIG. 1.

Coronal discharge electrodes 208 and coronal discharge electrodes 209 are utilized to assist in the formation of the ion distribution layers. These coronal discharge electrodes are illustrated in FIG. 3 as comprising pairs but one skilled in the art can readily see that there could be a plurality of these discharge electrodes and that they could have different physical configurations. Consider the operation of discharge electrodes 208. The function of these electrodes is to create negative ions for the negative air ion distribution 203 above embedded positive electrode 202. Discharge electrodes 208 accomplish this by injecting electrons into the air molecules resulting in negative air ions which are attracted to embedded positive electrode 202 through electrostatic attraction. Discharge electrodes 209 function in a similar manner but adsorb electrons from the air molecules resulting in positive ions which are attracted to the embedded negative electrode 201 and are thus added to positive air ion distribution 204.

The make-up of the ion distributions above both electrodes is described with respect to embedded positive electrode 202. The distribution of negative ions in ion distribution 203 is in two different layers of ions associated with the positive electrode 202. The layer of ions immediately adjacent to the surface is called the Stern layer. The ions of this layer are held to the charged surface by a combination of electrostatic attraction and specific adsorption forces. The thickness of this layer is assumed to be about equal to the ionic diameter of the adsorbed ions. The second layer of ions is the Gouy layer. The ions in the Gouy layer are acted upon only by electrostatic forces and thermal motions. The net charge density of the diffused ion atmosphere of the Gouy layer decreases exponentially with the distance from the Stern plane. The ions in the Stern layer are tightly held to the surface of the plastic insulation by the embedded positive electrode 202 and the adsorption forces. However, the ions in the Gouy layer have what is known as a plane of sheer above which they are reasonably free to move horizontally with respect to embedded positive electrode 202. The positive ions in positive air ion distribution 204 have a similar distribution.

Since the ions in the Gouy layer of both ion distributions 203 and 204 are free to move in the horizontal direction with respect to their respective embedded electrodes 202 and 201, the ions in both Gouy layers drift towards region 214. The movement of the ions in the distribution layers is caused by the electrostatic attractions that the ions have for ions of the opposite polarity. As the ions move towards region 214, ions of the same polarity as the human body are expelled from the appropriate embedded electrode and flow through plastic grill 200 into the air to an external ground point. For example, if the body is at a positive potential with respect to ground, the positive ions will flow through plastic grill 200. The remaining ions entering region 214 are combined with each other to form air molecules. Since the embedded electrodes are in plastic insulation, there can be no arcing across region 214; hence, the rate of recombinations is at a near steady state within region 214. The continuous flow of ions is desirable to prevent space charges from building up around the coronal discharge electrodes, thus preventing the formation of ions by the coronal discharge electrodes. In the above example, the negative ions are combined in positive ions within the region 214; however, a greater number of positive ions is being added to positive air ion distribution 203 to make up for the loss of positive ions out of the discharge unit 100 via plastic grill 200.

While a specific embodiment of the invention has been disclosed, variations in structural detail, within the scope of the appended claims, are possible and are contemplated. There is no intention of limitation to what is contained in the abstract or the exact disclosure as herein presented. The above-described arrangements are only illustrative of the application of the principles of the invention. Other arrangements may be devised by those skilled in the art without departing from the spirit and the scope of the invention.

I claim:

1. Apparatus for the static electric discharge of a body and which is worn on the body, comprising;
   a pair of embedded electrodes in a common horizontal plane;
   conductive body contact means for making an electrical contact with said body;
   a first voltage means connecting the negative terminal of said first voltage means to a first one of said embedded electrodes and the positive terminal of said first voltage means to said conductive body contact means;
   a second voltage means connecting a positive terminal of said second voltage means to a second one of said embedded electrodes and a negative terminal of said voltage means to said conductive body contact means;
   a first set of discharge electrodes connected to said first one of said embedded electrodes for generating negative air ions in the vicinity of said second one of said embedded electrodes thereby creating a distribution of negative ions in the vicinity of said second one of said embedded electrodes;
   a second set of discharge electrodes connected to said second one of said embedded electrodes for generating positive ions in the vicinity of said first one of said embedded electrodes thereby creating a positive air ion distribution in the vicinity of said first one of said embedded electrodes; and
   a recombination region of a predetermined width between said first and second ones of said embedded electrodes whereby the ions from said negative and positive air ion distributions horizontally move under electrostatic attraction from each other to said recombination region releasing ions of the same polarity of said body into the air to flow away from the embedded electrodes into the surrounding air thereby resulting in the removal of static electricity from said body.

2. The apparatus of claim 1 wherein said first and second voltage means are solar cell units for producing electricity from ambient light.

3. The apparatus of claim 2 further comprises a conductive wrist strap connected to said conductive body contact means thereby allowing the apparatus to be worn on the wrist of said body.

* * * * *